United States Patent [19]

Heath et al.

[11] 3,957,862

[45] *May 18, 1976

[54] METHOD OF MAKING AROMATIC BIS(ETHER ORTHO PHTHALIC ACID)S

[75] Inventors: Darrell R. Heath, Pittsfield, Mass.; Tohru Takekoshi, Scotia, N.Y.

[73] Assignee: General Electric Company, Schenectady, N.Y.

[ * ] Notice: The portion of the term of this patent subsequent to Apr. 22, 1992, has been disclaimed.

[22] Filed: Dec. 6, 1974

[21] Appl. No.: 530,184

Related U.S. Application Data

[63] Continuation of Ser. No. 346,473, March 30, 1973, Pat. No. 3,879,428.

[52] U.S. Cl. ............................................. 260/520 E
[51] Int. Cl.$^2$ ....................................... C07D 307/89
[58] Field of Search ....................... 260/346.3, 520 E

[56] References Cited
UNITED STATES PATENTS 3,787,475  1/1974  Heath et al. .................... 260/346.3

*Primary Examiner*—Natalie Trousof
*Assistant Examiner*—Bernard I. Dentz
*Attorney, Agent, or Firm*—William A. Teoli; Joseph T. Cohen; Jerome C. Squillaro

[57] ABSTRACT

Aromatic bis(ether anhydride)s can be made by a nitro displacement of an N-substituted nitrophthalimide with an alkali diphenoxide to produce an intermediate aromatic bis(etherphthalimide). Hydrolysis of the aromatic bis(etherphthalimide) to the corresponding tetra-acid salt followed by acidification and dehydration, results in the production of the aromatic bis(ether anhydride). These anhydrides can be used as intermediates for making polyimides. The intermediate aromatic bis(etherphthalimide) can be employed as a plasticizer in polyimide resins.

9 Claims, No Drawings

METHOD OF MAKING AROMATIC BIS(ETHER ORTHO PHTHALIC ACID)S

This is a continuation of application Ser. No. 346,473, filed Mar. 30, 1973 now U.S. Pat. No. 3,879,428.

The present invention relates to a method for making aromatic bis(ether anhydride)s from N-substituted nitrophthalimides by a nitro displacement reaction with bisphenolate, follwed by phthalimide ring openings to the tetra acid salt, acidification, and subsequent dehydration. The intermediate aromatic bis(etherimide) is also provided.

The aromatic bis(ether anhydride)s which can be made by the method of the present invention have the following formula, (I) 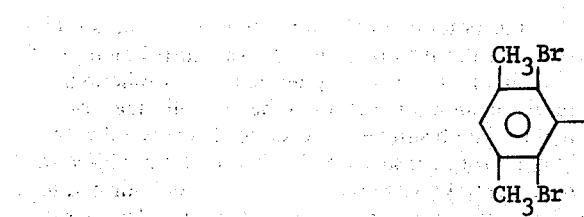

where R is a divalent aromatic radical having from 6–30 carbon atoms.

In accordance with the present invention the aromatic bis(ether anhydride)s of formula (I) can be made by (1) effecting nitro displacement of a nitrophthalimide of the formula, (II) 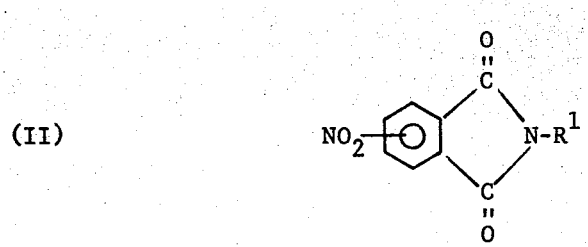

with an alkali diphenoxide of the formula,

M—O—R—O—M  (III)

to produce an intermediate aromatic bis(etherphthalimide), (2) hydrolyzing the aromatic bis(etherphthalimide) with base to produce a tetra-acid salt, (3) acidifying the tetra-acid salt to produce the tetra-acid, and (4) dehydrating the tetra-acid to the aromatic bis(ether anhydride) where R is as previously defined, M is a metal ion of an alkali metal selected from the class consisting of sodium, potassium, lithium, etc., and $R^1$ is a monovalent organo radical selected from the class consisting of $C_{(1-8)}$ alkyl radicals, and organic radicals having from 6 –20 carbon atoms, selected from the class consisting of aromatic hydrocarbon radicals and halogenated derivatives thereof.

Radicals included by R are more particularly

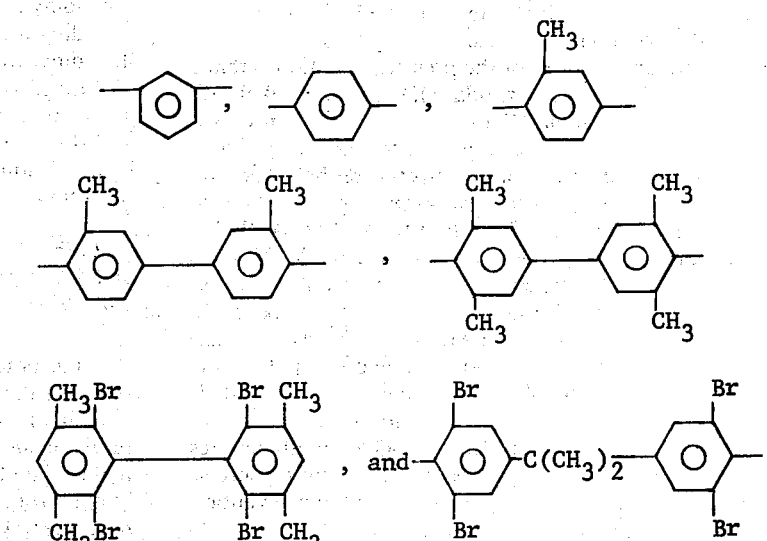

and (b) divalent organic radicals of the general formula

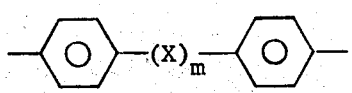

where X is a member selected from the class consisting of divalent radicals of the formulas,

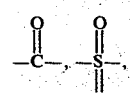

and —S—, where $m$ is 0 or 1, $y$ is a whole number from 1 to 5.

Radicals included by $R^1$ are, for example, phenyl, tolyl, xylyl, naphthyl, chlorophenyl, bromonaphthyl, etc., and alkyl radicals such as methyl, ethyl, etc.

The nitrophthalimides of formula II can be made by effecting reaction between substantially equal moles of nitrophthalic anhydride of the formula,

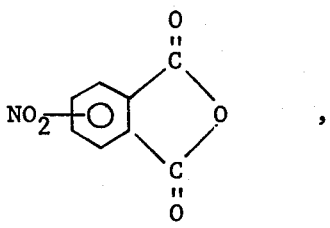

and an organic amine, $R^1 NH_2$, where $R^1$ is as previously defined in the presence of refluxing acetic acid. Included by such organic amines are, for example, aniline, toluidine, etc., methylamine, ethylamine, etc.. Nitrophthalimides included by formula (II) are, for example, N-phenyl-3-nitro-phthalimide, N-phenyl-4-nitrophthalimide, N-methyl-3-nitrophthalimide, N-butyl-4nitrophthalimide, etc.

A significant feature of the present invention is that a nitrophthalimide of formula (II) and an alkali diphenoxide of formula (III) can be reacted at from 5°C to 100°C and preferably ambient to 70°C to produce the corresponding aromatic bis(etherphthalimide) intermediate. This result is quite surprising in view of the teaching of Lyman R. Caswell in the Robert A. Welch Foundation Annual Report, Houston, Texas (1970), on page 58, which suggests a significant difference between the reactivities of 3- and 4-nitro-N-substituted phthalimides with sodium methoxide. A further advantage of the present invention is demonstrated by the teaching of German Offenlegungschrift No. 2,155,431, showing that temperatures of at least 150°C are required to couple N-substituted 4-chlorophthalimides with alkali metal dihydroxy cyclic compounds where as indicated above, the method of the subject invention allows for temperatures as low as 5°C.

Included by the aromatic bis(ether anhydride)s of formula (I), are compounds selected from where R is as previously defined. These dianhydrides can be employed to make polyetherimides which can be injection molded to useful products.

Included by the alkali metal salts of the above described alkali diphenoxides of formula (I) are sodium and potassium salts of the following dihydric phenols 2,2-bis-(2-hydroxyphenyl)propane;
2,4'-dihydroxydiphenylmethane;
bis-(2-hydroxyphenyl)methane;
2,2-bis-(4-hydroxyphenyl)propane hereinafter identified as "bisphenol-A" or "BPA";
1,1-bis-(4-hydroxyphenyl)ethane;
1,1-bis-(4-hydroxyphenyl)propane;
2,2-bis-(4-hydroxyphenyl)pentane;
3,3-bis-(4-hydroxyphenyl)pentane;
4,4'-dihydroxybiphenyl;
4,4'-dihydroxy-3,3,5,5'-tetramethylbiphenyl;
2,4'-dihydroxybenzophenone;
4,4'-dihydroxydiphenylsulfone;
2,4'-dihydroxydiphenylsulfone;
4,4'-dihydroxydiphenyl sulfoxide;
4,4'-dihydroxydiphenyl sulfide;
hydroquinone;
resorcinol;
3,4'-dihydroxydiphenylmethane;
4,4'-dihydroxybenzophenone;
and 4,4'-dihydroxydiphenylether.
2,4'-dihydroxybenzophenone;

In the practice of the invention, reaction is effected between the nitrophthalimide, or "nitroimide" of formula II, and the alkali diphenoxide or "diphenoxide" to produce an aromatic bis(etherphthalimide) or "bisimide". The bisimide is thereafter hydrolyzed with base to the tetra-acid salt, which is thereafter acidified to the tetra-acid; the tetra acid can then be dehydrated to the corresponding aromatic bis(ether anhydride) or "bisanhydride" of formula I.

(IV) 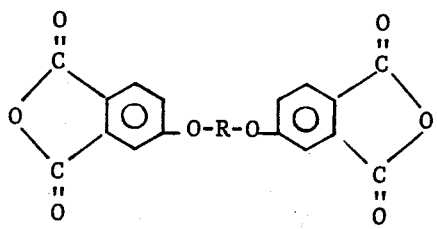

(V) 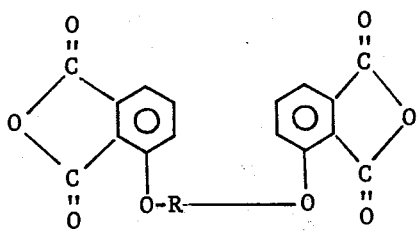

(VI) 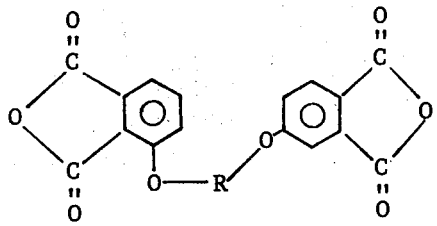

Reaction between the nitroimide and diphenoxide to produce the bisimide can be effected under an inert gas atmosphere such as nitrogen at 5°C to 100°C under substantially anhydrous conditions and in the presence of dipolar aprotic organic solvent such as dimethyl sulfoxide, N,N-dimethylformamide, N-methylpyrrolidine, N,N-dimethylacetamide, etc. Mixtures of such solvents with non-polar solvents such as toluene, chlorobenzene, etc. also can be employed. Reaction time can vary between 1 minute to 100 minutes or more depending upon temperature, degree of agitation, etc. A proportion of from 1.8 to 2.5 moles of nitroimide, per mole of diphenoxide can be used.

Hydrolysis of the bisimide to the tetra-acid salt can be effected under reflux conditions in the presence of a base such as an alkali hydroxide, for example, sodium hydroxide, etc. Reaction time can vary from 1 to 24 hours or more depending upon reactants, degree of agitation, temperature, etc. The organic amine by-product can be removed by standard procedures, such as steam distillation, etc. In addition, the rate of hydrolysis is greatly accelerated by carrying out the reaction at above atmospheric pressures at temperatures in the range of from 100° to 220°C.

The tetra-acid salt can thereafter be acidified with a mineral acid, such as a dilute aqueous solution of hydrochloric acid, etc. The resulting tetra-acid can be dehydrated by standard techniques. For example, refluxing with a dehydrating agent such as acetic anhydride, etc. the dianhydride can be recrystallized by standard procedures.

In order that those skilled in the art will be better able to practice the invention, the following examples are given by way of illustration and not by way of limitation. All parts are by weight.

EXAMPLE 1

A mixture of 2.28g (0.01 mol) ) of bisphenol-A, 30 ml of dimethylsulfoxide, 10 ml of benzene, and 0.8 g of sodium hydroxide as a 50% aqueous solution was stirred and heated to reflux in a nitrogen atmosphere over a Dean Stark trap for 5 hours. The benzene was distilled until the temperature of the reaction mixture exceeded 145°C and the mixture was cooled to 15°C. Then 5.36g (0.02 mol) of N-phenyl-3-nitrophthalimide and 20 ml of dimethylsulfoxide were added. The solution was stirred for 30 minutes at room temperature and 30 minutes at 50°C, cooled, and added to 600 ml of water. The gummy solid which separated was extracted into methylene chloride and the organic solution dried with sodium sulfate, filtered, and evaporated to leave an oil. The oil solidified when slurried with hot ethanol to give 5.6g (84% yield) of crude product. Recrystallization from acetonitrile gave fine white needles melting at 187°–188.5°C. Anal. Calcd. for $C_{43}H_{30}N_2O_6$: C, 77.0; H, 4.47; N, 4.18. Found: C, 77.1; H, 4.6; N, 4.2. Based on the above preparation and elemental analysis, there was obtained 2,2-bis[4-(N-phenylphthalimid-3-oxy)-phenyl]-propane.

A mixture of 81.5g of 2,2-bis[4-(N-phenylphthalimid-3-oxy)phenyl]propane, 200g of water and 160g of 50% sodium hydroxide was stirred at reflux for 12 hours. The mixture was steam distilled for 3 hours and then 250g of water were added and steam distillation was continued for 2 hours. Acidification of the homogeneous residue with hydrochloric acid caused the product to precipitate. The material was isolated by filtration and dried. There was obtained 66.7g of crude product. Anal. Calcd. for $C_{31}H_{24}O_{10}$: C, 66.9; H, 4.3. Found: C, 64.4; H, 4.5. Based on the above method of preparation and elemental analysis, there was obtained 2,2-bis[4-(2,3-dicarboxyphenoxy)-phenyl]propane.

A mixture of 45.9g of 2,2-bis[4-(2,3-dicarboxyphenoxy)phenyl]propane, 400 cc of glacial acetic acid, and 25 cc of acetic anhydride was stirred at reflux for 3 hours. There was obtained 34.2g of an off-white solid when the mixture was filtered. The product was recrystallized from toluene/acetic acid to give 30.0 30.0g of white needles; m.p. 186°–187.5°C. Anal. Calcd. for C $_{31}H_{20}O_8$: C, 71.5; H, 4.1. Found: C, 71.4; H, 3.8. Based on method of preparation and elemental analysis, the product was 2,2-bis[4-(2,3-dicarboxyphenoxy)-phenyl]propane dianhydride.

EXAMPLE 2

A mixture of 29.8g (0.131 mol) of bisphenol-A, 10.44g of sodium hydroxide in the form of a 50% aqueous solution, 250 cc of dimethylsulfoxide, and 66 cc of toluene was stirred in a nitrogen atmosphere at reflux for 7 hours. Final drying was effected by refluxing the toluene over a recirculating trap filled with calcium hydride. The toluene was removed by distillation and the reaction mixture was cooled to 60°C. Then 70.0g (0.26 mol) of N-phenyl-4-nitrophthalimide and 250 cc of dimethylsulfoxide were added; the resulting solution was stirred at 60°C for 45 minutes. There was added 25 cc of glacial acetic acid; the reaction mixture was then diluted with 1400g of water. A fine solid separated; it was isolated by filtration, washed with water, and dried. After recrystallization from acetonitrile and from benzene there was obtained 44.4g of white needles, m.p. 214°C. Anal. Calcd. for C $_{43}H_{30}N_2O_6$: C, 77.0; H, 4.51; N, 4.18. Found: C, 76.7; H, 4.5; N, 4.1. Based on method of preparation and elemental analysis the product was 2,2-bis[4-(N-phenylphthalimid-4-oxy)phenyl]-propane.

A mixture of 60.2g of 2,2-bis[4-(N-phenylphthalimid-4-oxy)phenyl]propane, 57.37g of an aqueous 50% sodium hydroxide solution, and 350 cc of water was heated for 25 hours at 160°–175°C under 150 psi pressure. The mixture was then steam distilled for 45 minutes. The aqueous residue was acidified with hydrochloric acid. A product separated from the aqueous solution, which was washed with water and recrystallized from 50% acetic acid. There was obtained 32.9g of product; m.p. 208°–215°C. Anal Calcd. for $C_{31}H_{24}O_{10}$: C, 66.9; H, 4.3. Found: C, 66.5; H, 4.4. Based on method of preparation and elemental analysis, there was obtained 2,2-bis[4-(3,4-dicarboxyphenoxy)phenyl]-propane.

A mixture of 24.7g (0.05 mol) of 2,2-bis[4-(3,4-dicarboxyphenoxy)phenyl]propane, 250 cc of glacial acetic acid, and 12.8g of acetic anhydride was stirred at reflux for 2.5 hours. The solution was concentrated on a rotary evaporator. A white crystalline product separated on cooling. The product was isolated by filtration, washed with cold acetic acid, and dried in vacuo. The material was recrystallized from a toluene/ acetic acid mixture to give 20g of product, m.p. 187°—190°C. Anal Calcd. for $C_{31}H_{20}O_8$: C, 71.5; H, 4.1. Found: C, 72.0; H, 3.8. Based on method of preparation and elemental analysis, the product was 2,2-bis[4-(3,4-dicarboxyphenoxy)phenyl]propane dianhydride.

EXAMPLE 3

A mixture of 1.10g (0.01 mol) of hydroquinone, 0.8g of sodium hydroxied as a 50% aqueous solution, 30 ml of dimethylsulfoxide, and 10 ml of benzene was stirred in a nitrogen atmosphere at reflux over a Dean Stark trap for 3 hours. The benzene was removed by distillation until the temperature of the reaction mixture exceeded 140°C; the mixture was then cooled to 15°C. There were added 5.36g (0.02 mol) of N-phenyl-3-nitrophthalimide, and 20 ml of dimethylsulfoxide. The solution was stirred for 20 minutes at 15°–20°C, 20 minutes at 30°C and for 20 minutes at 40°C. After cooling the reaction mixture, there was added thereto 400 ml of water. A crude product was isolated by filtration. The crude product was dissolved in 700 ml of boiling ethylene glycol and separated from the cold solution as fine white needles. The recrystallized product was dried in vauco at 110°C. There was obtained 3.8g (70% yield) of product, m.p. 312°–313°C. Anal. Calcd. for $C_{34}h_{20}N_2O_6$: C, 73.9; H, 3.62; N, 5.07. Found: C, 73.8; H, 3.9; N, 5.0. Based on method of preparation and elemental analysis the product was 1,4-bis(N-phenylphthalimid-3-oxy) benzene.

A mixture of 54.2g of 1,4-bis(N-phenylphthalimid-3-oxy)benzene, 54.4g of a 50% aqueous sodium hydroxide solution, and 100 cc of water was stirred at reflux for 24 hours. There was added with stirring at reflux and additional 200g of water. The mixture was stirred for 2 more days. The mixture was steam distilled. A product separated when the aqueous solution was acidified. The crude material was isolated by filtration to give 46.4g of product. The product was then mixed with 55 g of 50% sodium hydroxide and 500g of water. It was heated at 180°C for 2 hours under sealed conditions. Acidification of the cooled solution with concentrated hydrochloric acid gave 41.1g of crude product. Recrystallization from a 50/50 mixture of water-acetic acid gave 39.3g of white powder; m.p. 305°–315°C. The product was found to be the acetic acid adduct of 1,4-bis(2,3-dicarboxyphenoxy)benzene. Anal. Calcd. for $C_{22}H_{14}O_{10}\cdot 2CH_3COOH$: C, 55.92; H, 3.97. Found: C, 56.0; H, 4.1. Acid number: Calculated, 10.74 meq/g; Found, 10.4 meq/g.

A mixture of 39.3g (0.0901 mol) of 1,4-bis(2,3-dicarboxyphenoxy)benzene, 400 cc of glacial acetic acid, and 25 cc of acetic anhydride was stirred at reflux for 3 hours. The solution was cooled and filtered. Based on method of preparation, the product was 1,4-bis(2,3-dicarboxyphenoxy)benzene dianhydride.

EXAMPLE 4

A series of bisimides were prepared in accordance with the present invention by effecting the nitro-displacement of a nitrophthalimide of formula II, with an alkali diphenoxide fo formula III. The bisimides were included by the following formula, (VII) 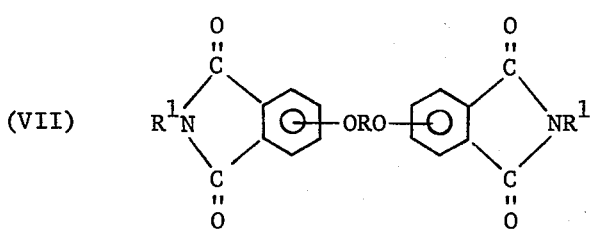

where R and $R^1$ are as previously defined.

The following tables show the bisimides prepared where R and $R^1$ are as defined in Table 1 and the calculated values for the elemental analysis are shown in Table 2.

TABLE 1.

Properties of Bisimides

| | R | $R^1$ | I.S.* | m.p. (°C) |
|---|---|---|---|---|
| (1) | 1,4-Benzene | n-Butyl | 3 | 187.5–188.5 |
| (2) | 1,3-Benzene | Phenyl | 3 | 270–272 |
| (3) | 4,4'-Biphenyl | Phenyl | 3 | 303–304.5 |
| (4) | 4,4'-Biphenyl | Phenyl | 4 | 311–313 |
| (5) | 4,4'-Diphenylether | Phenyl | 3 | 239.5–242.5 |
| (6) | 4,4'-Diphenylether | Phenyl | 4 | 305.5–308.5 |
| (7) | 4,4'-Diphenyl-sulfide | Phenyl | 3 | 284–285 |
| (8) | 4,4'-Diphenyl-sulfide | Phenyl | 4 | 229–230 |
| (9) | 2,2-Bis(4-phenyl)-propane | n-Butyl | 3 | 95–98 |
| (10) | 2,2-Bis(4-phenyl)-propane | n-Butyl | 4 | 88–90 |
| (11) | 4,4'-Benzophenone | Phenyl | 3 | 236.5–238.5 |
| (12) | 2,2-Bis(4-phenyl)-propane | Methyl | 3 | 208.5–209 |
| (13) | 2,2-Bis(4-phenyl)-propane | Methyl | 4 | 129–130 |

*Isomeric Structure

TABLE 2.

Elemental Analysis of the Above Bisimides

| | C | H (Calcd.) | N | S |
|---|---|---|---|---|
| (1) | 70.4 (70.3) | 5.5 (5.5) | 5.9 (5.5) | |
| (2) | 73.9 (73.9) | 3.7 (3.6) | 5.0 (5.1) | |
| (3) | 76.4 (76.4) | 4.0 (3.8) | 4.4 (4.5) | |
| (4) | 76.1 (76.4) | 3.9 (3.8) | 4.3 (4.5) | |
| (5) | 73.5 (74.5) | 3.8 (3.8) | 4.2 (4.4) | |
| (6) | 73.1 (74.5) | 3.9 (3.8) | 4.3 (4.4) | |
| (7) | 72.5 (72.7) | 3.5 (3.6) | 3.8 (4.2) | 4.8 (4.9) |
| (8) | 72.7 (72.7) | 3.8 (3.6) | 4.3 (4.2) | 5.0 (4.9) |
| (9) | 74.5 (74.3) | 6.4 (6.0) | 4.5 (4.4) | |
| (10) | 74.3 (74.3) | 6.1 (6.0) | 4.4 (4.4) | |
| (11) | 75.0 (75.0) | 3.9 (3.7) | 4.3 (4.3) | |
| (12) | 72.6 (72.5) | 4.7 (4.8) | 5.2 (5.1) | |
| (13) | 72.6 (72.5) | 4.7 (4.8) | 5.2 (5.1) | |

The above bisimides can be employed as plasticizers for organic polymers such as polyvinylchloride, polyimides, etc; these bisimides can withstand oxidation at high temperatures.

Although the above examples are limited to only a few of the very many bisimides which are provided by the present invention, it should be understood that the bisimides provided by the invention are broadly shown by formula VII.

In addition to the dianhydride shown by the above examples, it should be understood that the method of the invention broadly provides dianydride shown by formula I.

What we claim as new and desire to secure by Letters Patent of the United States:

1. A method for making an aromatic-bis(ether dicarboxylic acid) which comprises
   a. effecting the nitro displacement of a nitrophthalimide of the formula,

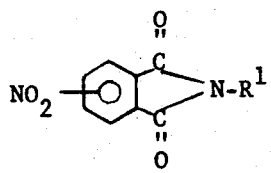

with an alkali diphenoxide of the formula,

to produce an intermediate aromatic-bis(etherphthalimide), (b) hydrolizing the aromatic-bis(etherphthalimide) of (a) with base to produce a tetra-carboxylic-acid-salt and (c) acidifying the tetra-carboxylic-acid salt to produce the corresponding tetra-carboxylic-acid, where R is a divalent aromatic radical having from 6–30 carbon atoms, M is an alkali metal ion, and $R^1$ is a monovalent organo radical selected from the class consisting of aromatic hydrocarbon radicals, halogenated aromatic hydrocarbon radicals and altyl radicals of 1—8 carbon atoms.

2. A method in accordance with claim 1 where the alkali diphenoxide is the diphenoxide of bisphenol-A.

3. A method in accordance with claim 1 where the alkali diphenoxide is the diphenoxide of hydroquinone.

4. A method in accordance with claim 1 where $R^1$ is phenyl.

5. A method in accordance with claim 1 where $R^1$ is methyl.

6. A method in accordance with claim 1 where M is sodium.

7. A method in accordance with claim 1 where N-phenyl-3-nitrophthalimide is used.

8. A method in accordance with claim 1 where N-phenyl-4-nitrophthalimide is used.

9. A method in accordance with claim 1 where a mixture of N-phenyl-3-nitrophthalimide and N-phenyl-4-nitrophthalimide is used.

* * * * *